(12) United States Patent
Nichols et al.

(10) Patent No.: US 7,067,303 B1
(45) Date of Patent: Jun. 27, 2006

(54) **CULTURE CONTAINING BIOMASS ACID HYDROLYSATE AND *CONIOCHAETA LIGNIARIA* FUNGUS**

(75) Inventors: Nancy N. Nichols, Danvers, IL (US); Maria J. Lopez, Vicar (ES); Bruce S. Dien, Peoria, IL (US); Rodney J. Bothast, East Peoria, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 159 days.

(21) Appl. No.: 10/350,591

(22) Filed: Jan. 24, 2003

(51) Int. Cl.
  *A01N 65/00* (2006.01)
  *A01N 65/04* (2006.01)
  *C02F 3/34* (2006.01)
  *C12N 1/20* (2006.01)
  *D06M 16/00* (2006.01)

(52) U.S. Cl. ............... 435/254.1; 424/93.5; 435/252.1; 435/256.8; 435/262; 435/264; 435/911

(58) Field of Classification Search ................ 435/243, 435/253.7; 424/93.1
See application file for complete search history.

(56) References Cited

U.S. PATENT DOCUMENTS 6,485,952 B1 * 11/2002 Bradley et al. ............. 435/195

* cited by examiner

*Primary Examiner*—David M. Naff
*Assistant Examiner*—Deborah K. Ware
(74) *Attorney, Agent, or Firm*—John D. Fado; Curtis P. Ribando; Lesley Shaw

(57) ABSTRACT

Agricultural biomass hydrolysate is detoxified by culturing in the presence of the fungus *Coniochaeta ligniaria* (teleomorph) or its *Lecythophora* (anamorph) state. This organism is capable of significantly depleting the toxicant levels of furans, particularly furfural and 5-hydroxymethylfurfural. A new strain of the fungus has been isolated and deposited in the Agricultural Research Culture Collection (NRRL) in Peoria, Ill., as Accession No. NRRL 30616. The detoxified agricultural biomass hydrolysate is useful as a substrate for industrial fermentation processes, especially in saccharification treatments for bioethanol production.

8 Claims, 4 Drawing Sheets

CULTURE CONTAINING BIOMASS ACID HYDROLYSATE AND *CONIOCHAETA LIGNIARIA* FUNGUS

BACKGROUND OF THE INVENTION

1. Field of the Invention

This invention relates to biological inhibitor abatement in the context of preparing agricultural biomass. Agricultural biomass, such as corn fiber or corn stalks, can be used as an abundant and low-cost substrate for bioethanol production [Bothast, R. J. and Saha, B. C. (1997) 44:261–286] or production of other value-added products. Sugars contained in the lignocellulosic matrix are first released by hydrolysis, and then fermented to ethanol or other value-added chemicals by microorganisms. Biomass is made up of xylan and celluose polymers that must be pretreated to release sugars, prior to fermentation. Several pretreatment methods have been proposed [Hsu, T. (1996) Pretreatment of biomass. In: Handbook on Bioethanol: Production and Utilization. Wyman C. E. (Ed). Washington, D. C.: Taylor and Francis]. Most use conditions that create inhibitors simultaneous-with the production of sugars. For example, the resultant hydrolysate from dilute acid pretreatment comprises a complex mixture of components, in which more than 35 potentially toxic compounds have been identified [Luo, C. et al. (2001) *Biomass Bioenergy* 22:125–138]. These compounds can be divided into three main groups: organic acids (acetic, formic and levulinic acids), furan derivatives (furfural and 5-hydroxymethylfurfural), and phenolic compounds. They derive from sugar degradation or are directly released from the lignocellulose polymer [Palmqvist, E. and Hahn-Hägerdal, B. (2000) *Biores. Technol.* 74:25–33]. They affect the overall cell physiology and often result in decreased viability, ethanol yields and productivity (Palmqvist and Hahn-Hägerdal, supra), and possibly total failure of the fermentation process. Although ethanologenic microorganisms may degrade some of these compounds, the toxicity of the hydrolysate will likely persist as a result of the aggregate effect of the remaining compounds [Zaldivar, J. et al. (2001) *Appl. Microbiol. Biotechnol.* 56:17–34].

2. Description of the Prior Art

Several approaches have been suggested for overcoming the negative effect of inhibitors in hydrolysates, including: the reduction of their formation by adjusting sugar extraction conditions; the use of tolerant ethanologenic strains; and hydrolysate detoxification (Zaldivar J. et al., supra).

The most established methods for hydrolysate detoxification include the addition of ion exchange resins [Nilvebrant, N. O. (2001) *Appl. Biochem. Biotechnol.* 91/93: 35–49], addition of active charcoal [Gong, C. S. et al. (1993) *Appl. Biochem. Biotechnol.* 39/40:83–88], enzymatic detoxification using laccase [Jönsson, L. J. et al. (1998) *Appl. Microbiol. Biotechnol.* 49:691–697] and overliming [Martinez, A. et al. (2001) *Biotechnol. Prog.* 17:287–293]. Notwithstanding their benefits, these methods have certain limitations [Zaldivar, J. et al., (1999) *Biotechnol. Bioeng.* 65:24–33]; namely, producing waste and/or adding significantly to the cost of production.

In contrast, microbiological abatement represents an improvement compared to the aforementioned approaches to detoxification. Biological abatement generates little waste, and it may be performed directly in the fermentation vessel prior to fermentation. However, to date, few biological treatment processes have been studied. Schneider [*Enzyme Microb. Technol.* 19:94–98 (1996)] proposed a treatment using a *S. cerevisiae* mutant for acetic acid removal from acid hydrolysate without altering sugars. Treatment with soft-rot fungus *Trichoderma reesei* that degrade inhibitors in a hemicellulase hydrolysate has also been reported [Palmqvist, E. et al. (1997) *Enzyme Microb. Technol.* 20:286–293].

SUMMARY OF THE INVENTION

We have now identified a fungus that has superior functionality for agricultural biomass hydrolysate detoxification. When cultured on biomass acid hydrolysate, the fungus *Coniochaeta ligniaria* (teleomorph) or its *Lecythophora* (anamorph) state is capable of significantly depleting the toxicant levels, especially the level of furans, including all, or nearly all, of the furfural and 5-hydroxymethylfurfural (5-HMF). A novel *Lecythophora* (or anamorph) state of *C. ligniaria* has been isolated that is useful for inhibitor abatement in hydrolyzed biomass.

It is an object of this invention to provide a fungal species for use in biological inhibitor abatement of agricultural biomass hydrolysate.

It is a further object of this invention to provide a novel fungal strain useful in biological inhibitor abatement.

It is a particular object of the invention to provide a method for dramatically reducing the levels of furans, including furfural and 5-HMF in acid hydrolyzed corn stover and other hydrolysates prepared from agricultural biomass.

Another object of the invention is to provide an efficacious and economical biomass substrate pretreatment for industrial fermentation processes, especially bioethanol production.

Other objects and advantages of this invention will become readily apparent from the ensuing description.

DEPOSIT OF BIOLOGICAL MATERIAL

Figure 1A:
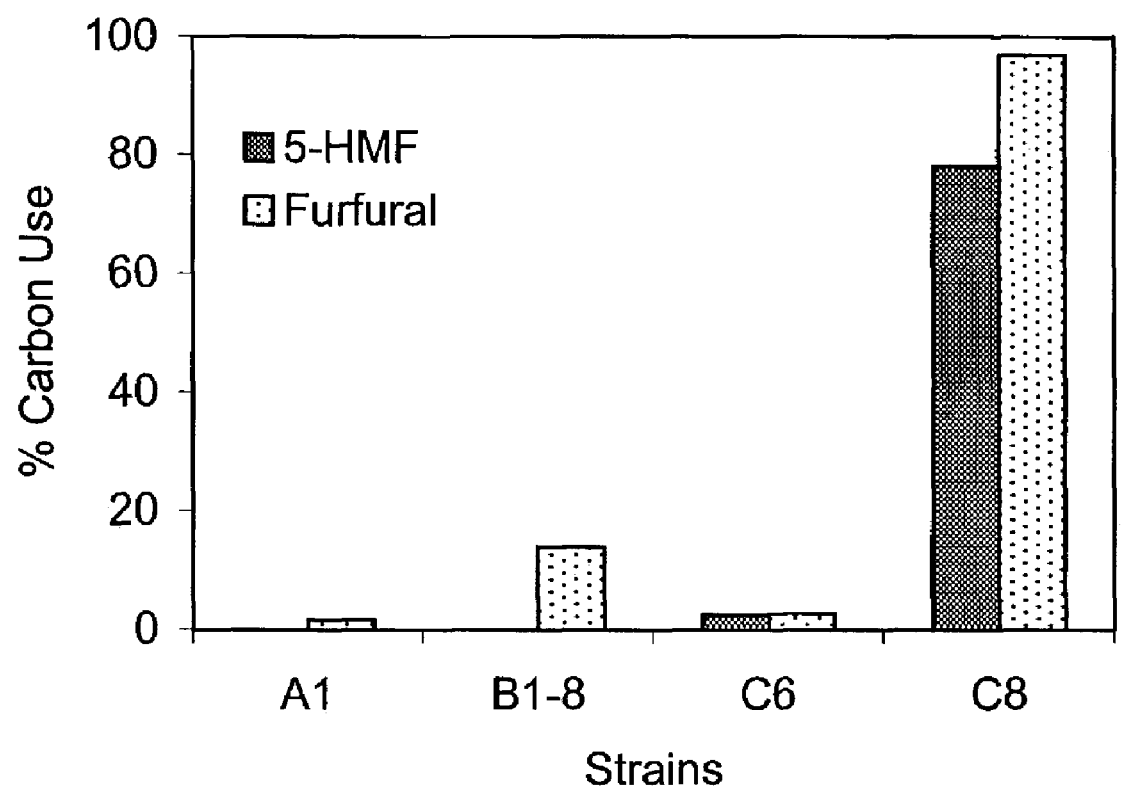
FIG. 1A compares the levels of 5-HMF and furfural removal in a liquid complex medium (corn stover hydrolysate with added nitrogen-CSH) by selected isolates.

Isolate C8, identified as a strain of *Lecythophora* (anamorph) state of *Coniochaeta ligniaria* (teleomorph), was deposited on Aug. 27, 2002, under the provisions of the Budapest Treaty in the Agricultural Research Culture Collection (NRRL) in Peoria, Ill., and has been assigned Accession No. NRRL 30616.

DETAILED DESCRIPTION

Agricultural biomass is defined herein to mean any cellulosic or lignocellulosic plant material, especially waste material, including but not limited to, leaves and stalks of both woody and non-woody plants. The term "woody" is used herein both in the botanical sense to mean "comprising wood"; that is, composed of extensive xylem tissue as found in trees and shrubs, and also in the sense of "being wood-like". Accordingly, "nonwoody" refers to materials lacking these characteristics.

Agricultural biomass from woody plants would include orchard prunnings, chaparral, mill waste (such as bark, chips, shavings, sawdust, and the like), urban wood waste (such as discarded lumber, wood pallets, crates, tree and brush trimmings, etc.), municipal waste (such as newspaper and discarded grocery produce), logging waste and forest thinnings (tree tops, limbs and cull material), short-rotation woody crops such as poplar and cottonwood, and industrial waste (such as wood pulp sludge).

The preponderance of biomass from non-woody plants is derived from monocotyledonous plants, and especially grassy species belonging to the family Gramineae. Of primary interest are gramineous agricultural residues; that is, the portion of grain-bearing plants that remain after harvesting the seed. Illustrative of such residues, without limitation thereto, are wheat straw, oat straw, rice straw, barley straw, rye straw, flax straw, sugar cane, corn stover, corn stalks, corn cobs, corn husks, and the like. Also included within this definition are grasses not conventionally cultivated for agricultural purposes, such as prairie grasses (e.g. big bluestem, little bluestem, Indian grass), gamagrass, and foxtail.

Other agricultural byproducts in the category of biomass include waste streams components from commercial processing of crop materials (such as sugar beet pulp, citrus fruit pulp, seed hulls, and the like), cellulosic animal wastes, lawn clippings, seaweed, etc.

Any of the aforementioned biomass materials would be useful herein as substrates for fermentative conversion to ethanol. The term "agricultural biomass hydrolysate" or variations thereof is used herein to refer to any of the aforementioned biomass materials that have been pretreated with acid to solubilize the xylan and cellulose in the material and to release sugar monomers. The hydrolysate may have residual xylan or may have been treated to remove the xylan prior to the detoxification treatment described hereafter.

One fungus of particular interest herein for detoxifying agricultural biomass hydrolysate is the newly-isolated C8 (NRRL 30616), most appropriately referred to as the Lecythophora anamorph of *C. ligniaria* based on molecular identification and growth morphology. C8 grows in the asexual state, and has not been observed to form sexual structures. C8 forms peach-colored filamentous colonies on solid YPD, potato dextrose, and corn meal medium.

In general, fungi useful for agricultural biomass hydrolysate detoxification in accordance with the invention include strains of *C. ligniaria* and closely related organisms. *C. ligniaria* is a filamentous fungus that inhabits the soil, plants and decaying wood. Exemplary strains other than C8 include NRRL 31961 (DSM 2693; ATCC 34158), NRRL 32068 (95.605; CBS110463), NRRL 32069 (98.1105; CBS110466), NRRL 32070 (98.1126), NRRL 32072 (F3343; F3374; CBS110468), and NRRL 32083 (CBS178.75).

For purposes of the invention, the expression "closely related organisms" may be defined in terms of DNA relatedness. Of particular interest herein is the relatedness of a rDNA sequence at the 5' end of the large subunit ribosomal RNA gene. For reference, this region corresponds to nucleotides 63–642 of the LS rDNA of *Saccharomyces cerevisiae* and is known as the D1/D2 domain of the large ribosomal subunit gene. This region is amplified with primers NL-1 and NL-4 as described by Kurtzman C. P. and Robnett C. J. [1998, *Antonie van Leeuwenhoek* 73:331–371]. For isolate C8, the sequence of this rDNA region is 602 nucleotides in length and is 100% identical to the corresponding sequences (available in GenBank) of aforementioned *C. ligniaria* strains NRRL 32068, NRRL 32069, NRRL 32070, and NRRL 32072, to the extent that they have been sequenced. Also, the sequence of C8 rDNA in this region is 98.9% identical to the aforementioned *C. ligniaria* strain NRRL 32083 and is estimated (based on relatedness of C8 to other strains of *L. hoffmannii*) to be 97–98% identical to the above-mentioned strain of *L. hoffmannii*, NRRL 31961. These data suggest that strains and species other than *C. ligniaria* that have rDNA relatedness in this region of at least 97%, at least 98%, and especially at least about 99%, would expectedly grow on, and utilize, a combination of furfural and 5-HMF.

When *C. ligniaria* is used as a detoxifier of acid-hydrolyzed agricultural biomass in accordance with the invention, it will advantageously metabolize a mixture of furans, including for example, furfural and 5-HMF. An additional advantage of this fungus is that it needs minimal or null nutrient supplementation to the hydrolysate. Secondary carbon sources for use in combination with the furans are, without limitation thereto include, glucose, sucrose, mannose, fructose, maltose, galactose, and the like. Starch is also useful as a secondary carbon source, provided that glucoamylase is introduced into the fermentation medium to promote saccharification during the course of the fermentation. The amount of secondary carbon source can be up to about 50% (w/w) of the total substrate, though it is preferred that the secondary carbon source constitute less about 33% of the carbon substrate. If sufficient nitrogen is not present in the biomass substrate, then the nitrogen should be supplemented with a suitable source such as $(NH_4)_2SO_4$. The level of nitrogen addition would typically be at least about 0.01% (w/v), and usually less than about 5% (w/v).

*C. ligniaria* may be maintained on any suitable culture medium such as yeast-peptone-dextrose (YPD) consisting of 10 g/l yeast extract, 20 g/l peptone, 20 g/l dextrose and 20 g/l agar.

Detoxification may be conducted by inoculating the hydrolyzed biomass material with sufficient *C. ligniaria* inoculum to initiate growth as readily determined by the person in the art. The detoxification is carried out under conditions conducive to the growth of *C. ligniaria*. Temperature of the substrate during detoxification should be maintained within the range of at least about 25° C., and less than about 40° C. Preferably, the temperature is at least about 30° C. and less than or equal to about 35° C. The pH of the medium at the commencement of the incubation is typically within the range of about 5.7–7.5. The detoxification is continued until the level of furans or other toxicants is reduced to a predetermined threshold. For instance, it would normally be desired to reduce each toxicant to less than 90%, 75%, 50%, 25%, 10% or 5% of its original level.

In one embodiment of the invention, the detoxification would be carried out as a separate preliminary step prior to saccharification. The recovered detoxified acid hydrolysate would subsequently be saccharified to produce ethanol or the like. It is also envisioned that the detoxification can be conducted concurrently with substrate saccharification by combining the acid-hydrolysate, *C. ligniaria* inoculum and the saccharification enzymes in the same reaction vessel.

The ability of *C. ligniaria* to degrade mixtures of acid hydrolysate toxicants, particularly combinations of furfural, 5-HMF, and ferulic acid is an unexpected finding, especially in view of the fact that microbiological degradation of mixtures of these compounds has not been previously reported. Given that these compounds have a synergistic toxic effect, identification of a microorganism capable of degradation of mixtures thereof is especially advantageous.

It is understood that the foregoing detailed description is given merely by way of illustration and that modifications and variations may be made therein without departing from the spirit and scope of the invention. All patents and publications cited herein are incorporated by reference.

EXAMPLES

Culture Media.

Yeast-Peptone-Dextrose (YPD) medium consisting of 10 g/l yeast extract, 20 g/l peptone, 20 g/l dextrose and 20 g/l agar was used for strain maintenance and microbial counts. This medium without agar was used for preinocula preparation.

Media with toxic compounds were prepared by adding the carbon source (see below), sterilized by filtration, to an autoclaved mineral basal medium (MBM). The MBM with a final pH of 6.8 consisted of $Na_2HPO_4$, 12.5 mM; $KH_2PO_4$, 12.5 mM; $(NH_4)_2SO_4$, 0.1% (w/v); and 1 ml/L MBM of Hutner's mineral base solution [Gerhardt, P. et al. (Eds) (1994) Methods for General and Molecular Bacteriology. Washington, D.C.: American Society for Microbiology].

Media for enrichment (MBM-TM) consisted of MBM and a mixture of furfural, 20 mM; 5-HMF, 15 mM; and ferulic acid, 5 mM. Where indicated, toxic compounds were included in the media as single carbon sources.

For isolation and maintenance of microorganisms, solid MBM medium containing 1.5% Noble agar (Difco, Detroit, Mich.) and either furfural, 5-HMF, or ferulic acid, or their mixture (MBM-0.05TM), each at 0.05% (w/v), was used.

A complex medium (CSH) containing corn stover hydrolysate (see below) and 0.1% (w/v) $(NH_4)_2SO_4$ sterilized by filtration was also used for enrichment.

Preparation of Corn Stover Hydrolysates (CSH).

Corn stover was field dried to 5% moisture and finely ground in a Willy mill. Hydrolysis was carried out in a 5 U.S. gallon stirred high-pressure reactor manufactured of Carpenter 20® alloy (Model 4555, Parr Company, Moline, Ill.) equipped with a PID temperature controller (Model 4842). A 7% (w/v) corn stover suspension was heated to 180° C. and sulfuric acid injected to a final concentration of 0.6% (v/v, total volume). The reactor was agitated with a dual pitch blade turbine impeller at 800 rpm. After 10 min hydrolysis the material was cooled to 50° C. in 10 min. The hydrolysate was stored at 4° C. before use. For media preparation, the hydrolysate was neutralized with $Ca(OH)_2$, centrifuged at 15,000×g for 20 min, and sterilized through a 0.2 micron pore size filter. The neutralized hydrolysate had the following composition: furfural, 14 mM; 5-HMF, 2 mM; ferulic acid, 2 mM; glucose, 21 mM; xylose, 80 mM; arabinose, 11 mM; acetic acid, 36 mM.

Example 1

Enrichment and isolation.

Microorganisms were isolated from soil samples obtained from the grounds of an industrial plant, in areas supposed to have a history of furfural contamination. Initial soil microbiota was analyzed by serial 10-fold dilutions in sterile saline solution (NaCl, 0.9% (w/v)) and plate counts on YPD medium and on MBM amended with 0.05% (w/v) of either ferulic acid, furfural, 5-HMF, or their mixture (MBM-0.05TM) with each compound at 0.05% (w/v) (ferulic acid, 2 mM, furfural, 5 mM, and 5-HMF, 4 mM).

Microorganism populations were selected by means of a two-step enrichment protocol. The first enrichment culture was performed in MBM-TM, which contained a "toxic mixture" of some of the main toxic compounds usually found in acid hydrolysates (ferulic acid, furfural, and 5-HMF). This enrichment was followed by an additional transfer into a complex medium composed of corn stover hydrolysate (CSH) containing $(NH_4)_2SO_4$ as an added nitrogen source.

Five grams of soil were suspended in 250 ml Erlenmeyer flasks with 95 ml of MBM-TM, with the mixture of furfural, ferulic acid and 5-HMF as the sole carbon and energy sources. This enrichment medium was incubated aerobically for 48 hours at 150 rpm and 30° C. Three sequential transfers of 5 ml enrichment culture into 50 ml fresh MBM-TM medium were each incubated for 96 hours. The last culture in MBM-TM was followed by an additional 5 ml transfer into 50 ml complex medium containing CSH. This enrichment culture was incubated for 96 hours at 150 rpm and 30° C.

Detoxification assays.

Analyses of biodetoxification efficacy of selected strains were carried out in defined media supplemented with the mixture of toxic compounds, and in complex medium (CSH). For biodetoxification assays in defined media, liquid cultures with 5 ml MBM containing either ferulic acid (5 mM), furfural (20 mM) or 5-HMF (15 mM) or their mixture (MBM-TM) were inoculated with an overnight culture of the selected microorganism grown on liquid YPD medium. Preinoculum was centrifuged and resuspended in MBM, so that the addition of a 1% (v/v) inoculum resulted in an optical density at 550 nm of 0.02. Cultures were incubated at 150 rpm and 30° C. Samples were taken after six days, and the concentration of each carbon source was determined spectrophotometrically.

Biodetoxification assays in complex medium were performed in 250 ml flasks containing 25 ml of CSH. Inocula were prepared as indicated above. Cultures were incubated for five days at 150 rpm and 30° C. Concentrations of furfural, 5-HMF, and ferulic acid were determined by high-pressure liquid chromatography (HPLC) analysis.

For media containing inhibitor mixtures, concentrations of furfural, 5-HMF, and ferulic acid were measured by HPLC. Samples were analyzed with an HPLC using an Econosphere C18 column (5 micron particle size, 250 mm×4.6 mm, Alltech Inc., Deerfield, Ill.) and a UV1000 ultraviolet detector (277 nm; Thermo Finnigan, San Jose, Calif.). Samples were run at ambient temperature, and eluted at 0.8 ml/min with a linear gradient of 5% to 100% acidified methanol (containing 0.25% acetic acid) run over 30 minutes. For media containing a single inhibitor, concentrations of furfural, 5-HMF, and ferulic acid were measured spectrophotometrically at 277, 283, and 308 nm, respectively, using a DU640 spectrophotometer (Beckman Instruments, Fullerton, Calif.). Concentrations of sugars and acetic acid were determined using an HPLC with an Aminex HPC-87H column (Bio-Rad, Richmond, Calif.) and RI-150 refractive index detector (Thermo Finnigan). Samples were run at 65° C. and eluted at 0.6 ml/min with 5 mM sulfuric acid.

Identification of isolates.

Isolates were identified by comparing ribosomal DNA gene sequences to known sequences using the GenBank Advanced Blast Search (NCBI, NIH, Washington, D.C.).

Bacterial 16S rDNA was amplified from cells of a single colony per reaction, using eubacterial primers and PCR conditions described by Whitehead and Cotta [*Anaerobe* 7:181–187 (2001)]. For fungal isolate C8, template DNA was obtained from a pure culture by vortexing cells in the presence of glass beads and phenol-chloroform, essentially as described for rapid purification of yeast DNA by Ausubel et al. [Eds., Current Protocols in Molecular Biology. New York: John Wiley & Sons, Inc. (1999)]. The 5' end of the ribosomal large subunit gene (the 26S D1/D2 domain) was PCR-amplified from C8 DNA with primers NL-1 and NL-4 and cycling parameters summarized by Kurtzman and Robnett [*Antonie van Leewenhoek* 73:331–371 (1998)]. The ribosomal small subunit gene was amplified with primers NS1 (5'GTAGTCATATGCTTGTCTC3', SEQ ID NO:1) and NS8A (5'CCTTCCGCAGGTTCACCTACGGAAACC3', SEQ ID NO:2). The internal transcribed spacer (ITS), a 601 bp region that spans the 5S rRNA gene, was amplified with primers ITS4 (5'TCCTCCGCTTATTGATATGC3', SEQ ID NO:3) and ITS5 (5'GGAAGTAAAAGTCGTAACAAGG3', SEQ ID NO:4). PCR products were cloned (pCR2.1TOPO, Invitrogen Life Technologies Corp, Carlsbad, Calif.) and the resulting plasmids were purified (Qiagen Inc., Valencia, Calif.). For rDNA cloned from bacterial isolates, approximately 400 bases from each end of the cloned 1.6 Kb inserts were sequenced with universal primers, using a cycle sequencing reaction kit (Applied Biosystems, Foster City, Calif.). The rDNA fragments from fungal isolate C8 (the cloned ITS region, 2148 bp small subunit gene, and 602 bp large subunit gene D1/D2 domain) were completely sequenced on both strands, using a combination of universal and custom primers.

Microbiota from Soil samples.

Soil samples were screened for microorganisms that grew on solid mineral basal medium supplemented with either furfural, 5-HMF, ferulic acid, or a mixture of all three compounds. The number of soil microorganisms recovered from growth on each medium was compared with microbial counts obtained on YPD medium. Direct counts on plates revealed the presence in soil of microorganisms capable of growing on furfural, 5-HMF and ferulic acid, either in a mixture or separately as the sole carbon and energy source. Most soil microorganisms grew on ferulic acid, about 58% of the total counts on YPD. The counts notably decreased on media containing furans, and were lower on 5-HMF (2.6%) than on furfural (9.9%). The lowest microbial numbers were obtained in media that contained a mixture of all three carbon sources (MBM-0.05TM); these accounted for less than 1% of the total counts obtained on YPD.

Selection and identification of microorganisms.

The isolation of microorganisms for inhibitor abatement was performed at three different levels: directly from furfural-contaminated soil (collection A), from the last of three serial transfers on defined enrichment medium MBM-TM (collection B), and from a subsequent enrichment in corn stover hydrolysate (collection C) (Table 1). Most isolates were obtained from enrichment in MBM-TM.

Colonies with different morphology were chosen from either YPD or MBM-0.05TM plates, resulting in a total of 74 strains isolated either directly from soil or from the enrichment cultures (Table 1).

In order to select the microorganisms capable of growth on each of the three carbon sources as well as their mixture, each isolate was inoculated on plates containing the individual compounds and their mixture. After this analysis was performed, 29 isolates were chosen. These isolates were maintained on agar slants of MBM-0.05TM medium, but after three to four transfers, more than half of them lost the ability to grow on this substrate. There was a final set of 12 isolates with stable growth on MBM-0.05TM (Table 1).

The twelve selected isolates were subjected to molecular identification as described previously. This analysis revealed that the 26S rDNA sequence obtained from one of the isolates, fungal strain C8 (GenBank Accession No. AY198388), matched perfectly the reported sequence of Coniochaeta ligniaria [E. Weber et al. (2002) *Nova Hedwigia* 74:187–200]. Isolate C8 forms peach-colored filamentous colonies on solid YPD, potato dextrose, and corn meal medium. After one month of growth on these media, only immature fruiting bodies were observed, and no teleospores were present. This is consistent with the description of the Lecythophora anamorph of *Coniochaeta ligniaria* [E. Weber (2002) *Nova Hedwigia* 74:159–185].

The rDNA sequences for the bacterial isolates are available from GenBank with Accession Nos. AY198380-AY198387. Three of the strains, A3, A6, and B1—1, matched with *Pseudomonas* sp. (98–99% rDNA sequence identity). Strain A1 was most similar to *Methylobacterium extorquens* (98%), A5 to *Arthrobacter aurescens* (98%), C6 to *Flavobacterium indologenes* (95%), and C7 to *Stenotrophomonas maltophylia* (99%). The rDNA sequence of isolate B1-8 shared 99% identity with an unidentified *Acinetobacter*-like species. Sequences were not obtained for strains B1-9, B2-13, and C9.

Example 2

Detoxification in defined medium.

Further selection criteria in regard to the 12 selected isolates described in Example 1 involved the analysis of the depletion of toxic carbon sources from liquid media by the isolates. This analysis was performed in liquid media with either furfural (20 mM), 5-HMF (15 mM) or ferulic acid (10 mM), separately. The compounds were degraded at different rates for each strain. After 6 days, all 12 isolates degraded ferulic acid, seven isolates (A1, A6, B1—1, B1-9, C6, C7 and C8), depleted greater than 70% of 5-HMF and only two strains (B1-8 and C6) removed almost all of the furfural, when the compounds were supplied individually. Six of the twelve strains (C6, C8, B1-1, B1-8, A1 and A5) grew on the mixture of toxic compounds, based on optical densities measured in liquid media, and growth on solid media. Some of these six isolates did not grow on furans in media with such compounds as the single carbon source, but they were selected because of their ability to grow on at least one of the carbon sources in the presence of the mixture of toxic compounds.

Detoxification of CSH.

Figure 1B:
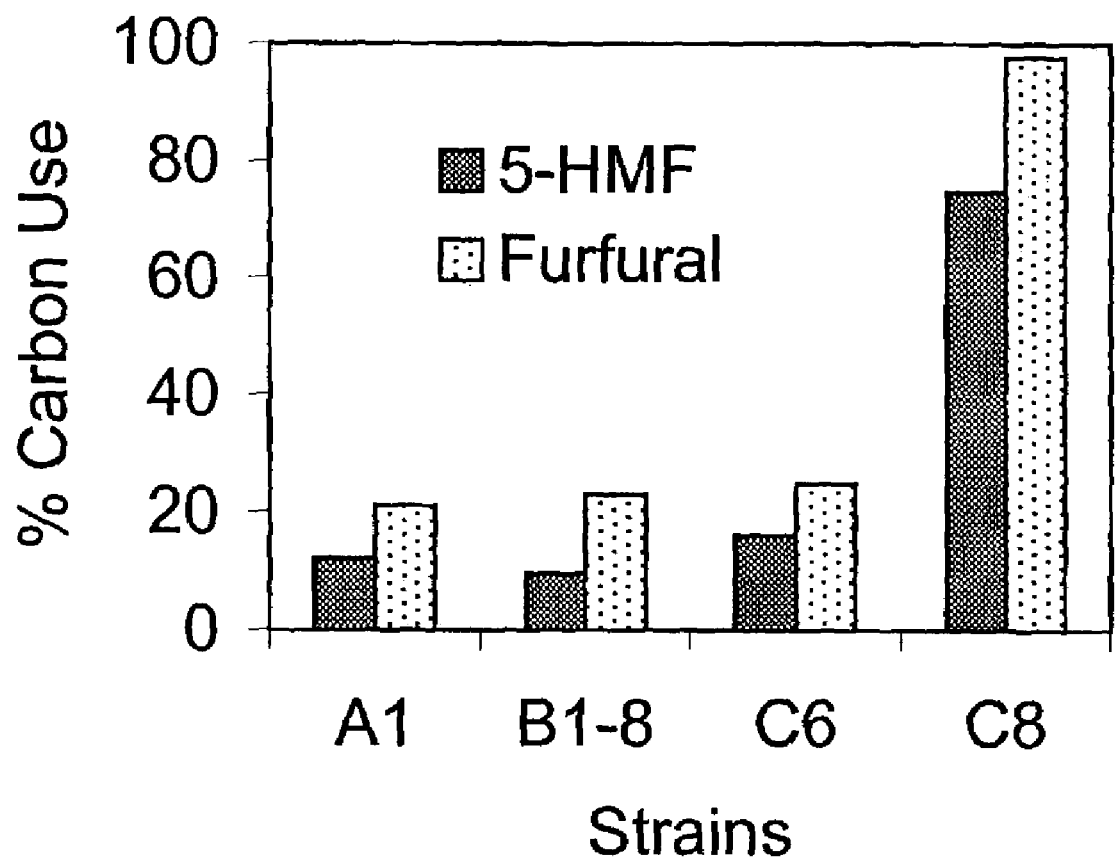
FIG. 1B compares the levels of 5-HMF and furfural removal in a liquid complex medium (50% diluted corn stover hydrolysate with added nitrogen-CSH) by selected isolates.

Four of the six selected microorganisms grew on corn stover hydrolysate (CSH), but only the fungus C8 depleted significant amounts of toxic compounds after five days culture (FIG. 1A). This fungal isolate used more than 80% of the furfural and 5-HMF from CSH. When the CSH was diluted 50%, the other three strains also grew and metabolized the toxic compounds, but to a lesser extent than C8 (FIG. 1B).

Figure 2:
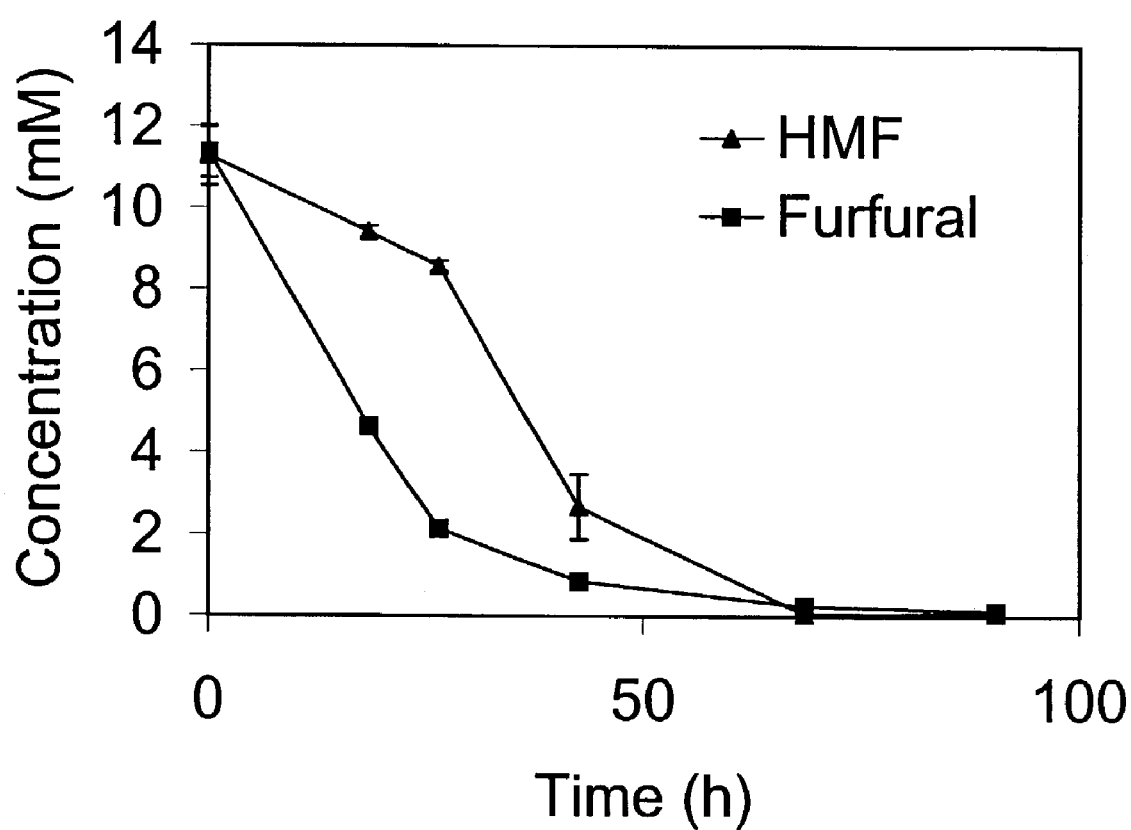
FIG. 2 is a time course of 5-HMF and furfural removal by isolate C8 of the invention on MBM-TM (mineral basal medium containing a toxic mixture of furfural, 20 mM; 5-hydroxymethylfurfural (5-HMF), 15 mM; and ferulic acid, 5 mM). I-bars depict the standard errors.
Figure 3:
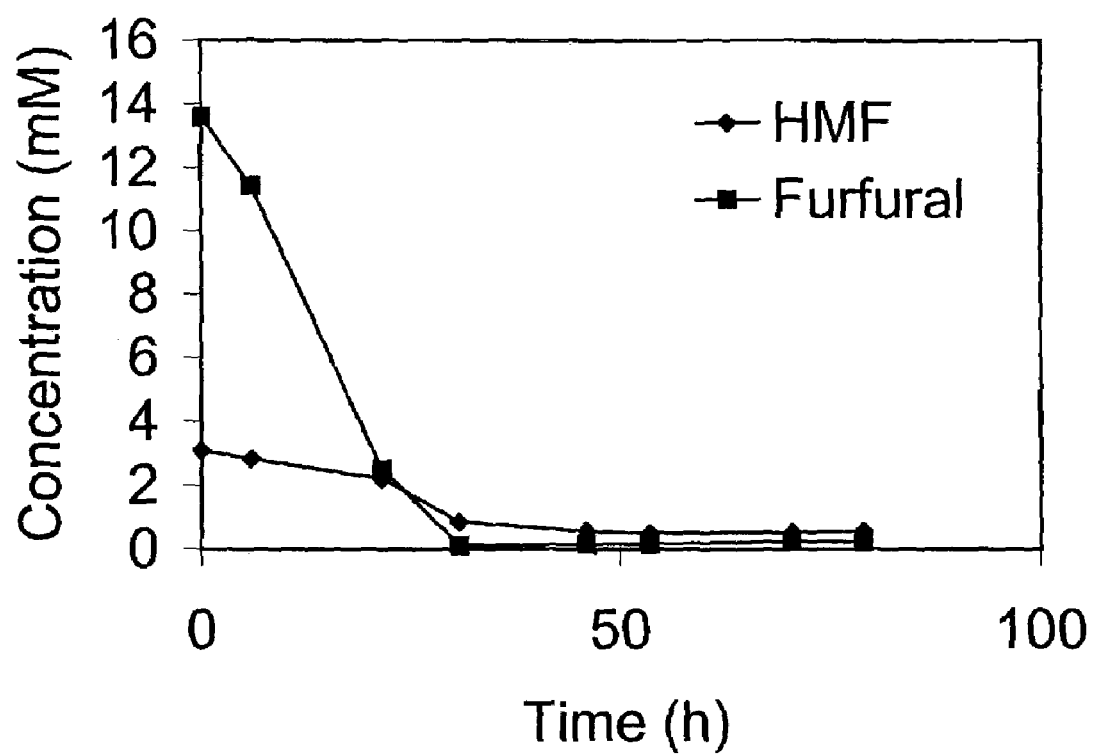
FIG. 3 is a time course of 5-HMF and furfural removal by isolate C8 of the invention on CHS.

Strain C8 was deposited on Aug. 27, 2002, under the provisions of the Budapest Treaty in the Agricultural Research Culture Collection (NRRL) in Peoria, Ill., and has been assigned Accession No. NRRL 30616. This strain completely depleted a mixture of furfural and 5-HMF from defined medium after 70 hours culture (FIG. 2). The time required to metabolize furfural and 5-HMF decreased in CSH medium, where consumption of furans was achieved after 30 hours culture (FIG. 3).

TABLE 1

Pre-Selection of Strains: Capability to grow on plates with separated compounds (Furfural, 5-HMF and Ferulic acid) and their mixture (TM) as sole carbon sources

| Origin | Collection Name | Total Isolates | Growth on plates with toxic compound at 0.05% | | | | | Maintain on TM† |
| --- | --- | --- | --- | --- | --- | --- | --- | --- |
| | | | Furfural | 5-HMF | Ferulic | TM | All* | |
| Soil | A | 17 | 16 | 15 | 15 | 13 | 7 | 4 |
| Enrichment Defined Medium (MBM-TM) | B | 48 | 23 | 24 | 27 | 24 | 18 | 4 |
| Enrichment Complex Medium (CSH) | C | 9 | 7 | 8 | 7 | 6 | 4 | 4 |
| Total | | 74 | 46 | 47 | 49 | 43 | 29 | 12 |

*Number of isolates that grow on plates with each toxic compound and also on their mixture
†Number of isolates that do not lose the ability to grow on plates with TM

We claim:

1. A culture comprising agricultural biomass acid hydrolysate and a strain of fungus *Coniochaeta ligniaria* (teleomorph) or its *Lecythophora* (anamorph) state, wherein said hydrolysate comprises a furan and wherein said fungus is capable of reducing the level of said furan.

2. The culture of claim 1, wherein said fungus has Accession No. NRRL 30616.

3. The culture of claim 1, wherein said agricultural biomass is a woody material.

4. The culture of claim 3, wherein said woody material is cellulosic or lignocellulosic plant material selected from the group consisting of orchard prunnings, chaparral, mill waste, urban wood waste, municipal waste, logging waste, forest thinnings, short-rotation woody crops, and industrial waste.

5. The culture of claim 1, wherein said agricultural biomass is a nonwoody material.

6. The culture of claim 5, wherein said nonwoody material is gramineous agricultural residue.

7. The culture of claim 5, wherein said nonwoody material is selected from the group consisting of wheat straw, oat straw, rice straw, barley straw, rye straw, flax straw, sugar cane, corn stover, corn stalks, corn cobs, corn husks, prairie grass, gamagrass, and foxtail.

8. The culture of claim 5, wherein said nonwoody material is selected from the group consisting of sugar beet pulp, citrus fruit pulp, seed hulls, cellulosic animal wastes, lawn clippings, and seaweed.

\* \* \* \* \*

SEQUENCE LISTING

<160> NUMBER OF SEQ ID NOS: 4

<210> SEQ ID NO 1
<211> LENGTH: 19
<212> TYPE: DNA
<213> ORGANISM: Coniochaeta ligniaria

<400> SEQUENCE: 1
gtagtcatat gcttgtctc                                                                 19

<210> SEQ ID NO 2
<211> LENGTH: 27
<212> TYPE: DNA
<213> ORGANISM: Coniochaeta ligniaria

<400> SEQUENCE: 2
ccttccgcag gttcacctac ggaaacc                                                         27

<210> SEQ ID NO 3
<211> LENGTH: 20
<212> TYPE: DNA
<213> ORGANISM: Coniochaeta ligniaria

<400> SEQUENCE: 3
tcctccgctt attgatatgc                                                                20

<210> SEQ ID NO 4
<211> LENGTH: 22
<212> TYPE: DNA
<213> ORGANISM: Coniochaeta ligniaria

<400> SEQUENCE: 4
ggaagtaaaa gtcgtaacaa gg                                                             22